United States Patent [19]

Bielmeier et al.

[11] Patent Number: 5,215,952
[45] Date of Patent: Jun. 1, 1993

[54] MACROPOROUS OXIDATION CATALYST AND METHOD FOR MAKING THE SAME

[75] Inventors: Ernst Bielmeier, Griesheim; Thomas Haeberle, Einhausen, both of Fed. Rep. of Germany

[73] Assignee: Röhm GmbH, Darmstadt, Fed. Rep. of Germany

[21] Appl. No.: 873,373

[22] Filed: Apr. 24, 1992

[30] Foreign Application Priority Data

Apr. 25, 1991 [DE] Fed. Rep. of Germany ....... 4113423

[51] Int. Cl.$^5$ .................... B01J 27/18; B01J 27/19; B01J 27/198
[52] U.S. Cl. ......................................... 502/209
[58] Field of Search ........................................ 502/209

[56] References Cited

U.S. PATENT DOCUMENTS

| | | | |
|---|---|---|---|
| 4,092,269 | 5/1978 | Mount et al. | 252/435 |
| 4,146,574 | 3/1979 | Onoda et al. | 423/299 |
| 4,329,520 | 5/1982 | Kavasmaneck et al. | 568/896 |
| 4,652,673 | 3/1987 | Matsumoto et al. | 562/535 |
| 4,720,575 | 1/1988 | Gruber | 560/214 |
| 4,804,778 | 2/1989 | Oh-Kita et al. | 502/209 X |
| 4,966,877 | 10/1990 | Langerbeins et al. | 502/209 |
| 4,968,877 | 10/1990 | Langerbeins et al. | 502/209 |

FOREIGN PATENT DOCUMENTS

| | | |
|---|---|---|
| 10005769 | 4/1982 | European Pat. Off. |
| 10113084 | 2/1986 | European Pat. Off. |
| 0237240 | 9/1987 | European Pat. Off. |
| 10255639 | 5/1989 | European Pat. Off. |
| 10376117 | 7/1990 | European Pat. Off. |
| 1805386 | 10/1968 | Fed. Rep. of Germany. |
| 1803773 | 7/1969 | Fed. Rep. of Germany. |
| 2722375 | 12/1977 | Fed. Rep. of Germany. |
| 3010434 | 11/1980 | Fed. Rep. of Germany. |
| 13145091 | 5/1983 | Fed. Rep. of Germany. |
| 3508649 | 9/1986 | Fed. Rep. of Germany. |
| 0284947 | 10/1988 | Fed. Rep. of Germany. |
| 60-150834 | 8/1985 | Japan ................... 502/209 |
| 1238207 | 7/1971 | United Kingdom. |

Primary Examiner—W. J. Shine

[57] ABSTRACT

Method for making catalysts for gas phase oxidation reactions by admixing a catalytically active material comprising oxides of molybdenum, phosphorus, and vanadium with combustible natural or synthetic fibers, or with carbon fibers, forming shaped bodies from the mixture, and then calcining said shaped bodies at 100° C. to 380° C. in oxygen, whereby said fibers are burned out to leave channels in said shaped bodies; catalysts made by such methods; and methods for gas phase oxidation reactions using such catalysts.

8 Claims, No Drawings

MACROPOROUS OXIDATION CATALYST AND METHOD FOR MAKING THE SAME

FIELD OF THE INVENTION

The present invention pertains to improved catalysts for the gas phase oxidation of organic compounds, to methods for making such catalysts, and to methods for using such catalysts in gas phase oxidation reactions. In particular, the catalysts contain oxidic Mo, P, and V and are useful for the preparation of unsaturated aldehydes and unsaturated carboxylic acids, above all for the preparation of methacrolein and methacrylic acid.

STATE OF THE ART

Catalysts of the oxidic kind, which contain molybdenum, phosphorus, and vanadium as essential elements, are particularly known as heteropolyacid catalysts for performing selective oxidations for the preparation of unsaturated aliphatic compounds such as acrolein, methacrolein, acrylic acid and methacrylic acid. Thus, for example, according to DE-OS 27 22 375 (=U.S. Pat. No. 4,146,574, incorporated herein by reference), catalysts containing the heteropolyacid $H_5PMo_{10}V_2O_{40}$ are used both for the oxidation of methacrolein to methacrylic acid and also for the oxydehydrogenation of isobutyric acid or its esters to methacrylic acid or its esters. According to EP-B 0 005 769, catalysts of the formula $Mo_aV_bP_cX_dO_e$, which have the heteropolyacid structure, are used for the oxidation of isobutylene and/or tert.-butanol to methacrolein and methacrylic acid. A method for the oxidation of methacrolein to methacrylic acid on catalysts of the same kind is described in DE-OS 30 10 434 (=U.S. Pat. No. 4,652,673, incorporated herein by reference).

The heteropolyacid of the formula $H_aPMo_{10}VO_{39}$, or its anhydride $PMo_{10}VO_{35}$, is, according to DE-OS 35 08 649 (=U.S. Pat. No. 4,720,575, incorporated herein by reference), suitable as a catalyst in oxidation reactions such as oxidation of the olefins propylene or isobutylene to the corresponding unsaturated aldehydes acrolein or methacrolein, and also for the further oxidation of these compounds to acrylic acid and methacrylic acid, and is particularly suitable in oxydehydrogenation reactions of isobutyric acid or its esters to methacrylic acid or its esters, and particularly in oxydehydrogenation reactions of isobutyric acid or its esters to methacrylic acid or its esters. According to EP-B 0 113 084, copper derivatives of this heteropolyacid anhydride, e.g. $Cu_{0.2}PMo_{10}VO_{35.2}$, and also those of other heteropolyacids, such as the $H_5PMo_{10}V_2O_{40}$ heteropolyacids, are selective catalysts in the oxydehydrogenation of isobutyric acid to methacrylic acid.

The preparation of molybdenum heteropolyacid oxidation catalysts of the kind described is reported in DE-OS 37 10 784 (=U.S. Pat. No. 4,966,877, incorporated herein by reference), according to which water soluble, practically non-volatile organic compounds, particularly polymers, are used. The catalysts are then calcined at 150° C. to 400° C. in the presence of oxygen. Catalysts prepared in this way excel in the oxydehydrogenation of isobutyric acid to methacrylic acid because of an improved long term behavior.

Finally, EP-A 0 376 117 proposes a method for making methacrylic acid by the oxidation of methacrolein on oxidic catalysts of the formula $Mo_{12}P_aV_bCs_cAs_d$-$Cu_eX_fY_gO_x$, during the shaping of which forming auxiliaries and strengthening agents, such as microfibers of inorganic materials like glass or asbestos for example, can be added in addition to known carbon-containing compounds functioning as lubricants. The catalysts are calcined at temperatures from 180° C. to 480° C., optionally in an atmosphere of air.

Catalysts for selective oxidation generally have a small interior surface area, i.e. the catalyst granule is supplied with relatively few pores, or, on the other hand, they are prepared using porous carriers having extensive pores in the interior of the carrier, in which pores the catalytic material is then embedded. Such carriers are readily permeable to a diffusion stream transporting material and energy to the catalytically active material. Combinations of materials containing molybdenum, vanadium, phosphorus, and oxygen, and carriers having a porosity of 10 to 80 percent and an interior surface area less than 1 m²/g are described as catalysts for the oxydehydrogenation of isobutyric acid to methacrylic acid in DE-OS 31 45 091.

The efficacy of catalysts in gas phase oxidation methods depends on a number of factors. Among these are the differences discussed above, such as the composition of the catalytically active species, the composition of the gas mixture to be reacted, or the reaction conditions, particularly the reaction temperature. However, catalyst efficacy also depends on an optimum number of pores with an optimum pore size distribution in the catalytically active material itself, according to which yield values and selectivity values of the desired product are determined, as well as the catalyst life. In the manufacture of catalysts, i.e. in forming them into shaped bodies, the active components, optionally in the presence of carrier materials or inert inorganic diluents, are compressed into pellets or extruded into rod-like particles, whereby a catalyst is made which, because of the extreme lack of porosity, essentially acts catalytically only by means of the material present on the surface. This particularly results in low space-time-yields and in a short catalyst life. On the other hand, catalysts which are prepared with carriers having high interior surface areas, such as discussed above and shown in DE-OS 31 45 091 for the oxydehydrogenation of isobutyric acid to methacrylic acid, show decreasing yield and selectivity values as the interior surface area increases.

PROBLEM AND SOLUTION

The present invention has as its object the manufacture of improved oxidation catalysts in the form of shaped bodies having good strength, particularly oxidic-type catalysts which contain molybdenum, phosphorus, and vanadium as essential elements and which are, above all, useful for the preparation of unsaturated aldehydes and unsaturated carboxylic acids having 3 or 4 carbon atoms. These new catalysts, because of their porous nature, have higher catalytic activities which are expressed by higher space-time-yields as well as in higher selectivities.

This object is achieved according to the invention by the manufacture of the catalysts by shaping mixtures of catalyst components with carbon fibers or organic fibers, present in amounts from 0.5 to 5 percent by weight of the catalytically active material, and then calcining the shaped catalyst bodies in a temperature region of 100° C. to 380° C., whereby transport channels are introduced.

The present invention thus concerns gas phase oxidation catalysts consisting of a catalytically active material which contains molybdenum, phosphorus, and vanadium as essential elements in oxidic form, and which may also comprise chemically inert inorganic binders, diluents, or carriers, as well as essentially uniformly distributed channels, wherein a catalytically active material of the chemical composition $H_aM_bP_cMO_dV_eO_f$, where M is at least one metal ion of Li, Na, K, Rb, Cs, Mg, Ca, Zn, Al, Ce, Ti, Zr, Sn, Sb, As, Bi, Cr, Mn, Fe, Co, Ni, or Cu a = 0 to 8
b = 0 to 6
c = 1 to 2
d = 9 to 12
e = 0.2 to 3 and
f = the number of atoms required for stoichiometric satisfaction of the other components based on their valences and amounts, or a precursor thereof, which material may optionally contain inert additives, is mixed with 0.5 to 5 percent by weight, based on the catalytically active material, of carbon fibers or organic fibers having a diameter from 1 to 100 microns and a length of 1 to 30 mm. After forming of this mixture into shaped bodies, the fibers are removed by calcination of the shaped bodies at a temperature in the region from 100° C. to 380° C. in the presence of oxygen, whereby channels are formed in the shaped catalyst bodies.

Materials of the chemical composition $H_aM_bP_cMo_dV_eO_f$ as defined above and having outstandingly good catalytic properties are especially heteropolyacids of molybdenum having phosphorus as the central atom, such as $H_5PMo_{10}V_2O_{40}$, $H_4PMo_{11}VO_{40}$, or their salts.

Catalysts prepared in this way are, as is necessary and conventional for oxidation catalysts, structures poor in surface area, i.e. their interior surfaces are in the range from about 0.1 to 5 m²/g, especially in the region from 0.5 to 2.5 m²/g, i.e. about in the order of magnitude of 1 m²/g. This means that the new process conditions form channels which are necessary for improved material and energy transport and, thereby, the reducing of inhibited diffusion, but do not significantly increase the interior surface area of the catalysts. The choice of the diameter, length, and amount of the destructible fibers added makes it possible to maintain the interior surface of the catalysts according to the invention in the necessary region indicated.

These new catalysts are advantageously useful in the oxidation of olefins such as propylene or isobutylene or their derivative, tert.-butanol, to the corresponding aldehydes, acrolein and methacrolein, and to their further oxidation to the unsaturated acids, acrylic acid or methacrylic acid. They are further especially useful for the oxydehydrogenation of isobutyric acid or its esters to methacrylic acid or its esters.

For the hydrogenating treatment of heavy oils, shaped catalysts which consist of carriers and active catalyst components are known from DE-OS 18 03 773 and EP-A 237,240, in the manufacture of which added organic textile fibers or carbon fibers in amounts of 10 percent by weight to about 20 percent by weight, based on the catalyst mass used, are removed by calcination in air at temperatures above 400° C., such as at temperatures of 400° C. to 1600 ° C. or at temperatures of 500° C. to 800° C., whereby catalyst having many channels arise. These catalysts have large interior surfaces, i.e. such as from 100 to 400 m²/g. Catalysts of this known kind are not usable for the preparation of unsaturated $C_3$- and $C_4$- aldehydes and carboxylic acids, especially of methacrylic acid or its esters in oxidation or oxydehydrogenation methods.

PERFORMING THE INVENTION

Active Components of the Catalyst

The catalysts of the invention and the catalysts used according to the invention contain as active materials substances which contain molybdenum, phosphorus, vanadium, and optional further elements, particularly metals, as an oxidic unit, and which correspond to the chemical composition $H_aM_bP_cMo_dV_eO_f$, where M, a, b, c, d, e, and f have their earlier meaning. These catalytically active substances are, as described in the state of the art, mostly phosphorus-molybdenum-heteropolyacids, particularly of their vanadium derivative, which can be described by the chemical formula $H_{3+x}PMo_{12-x}V_xO_{40}$, with x=0, 1, 2, 3, or the $H_8PMo_{10}VO_{39}$ heteropolyacid or its anhydride $PMo_{10}VO_{35}$, as well as metal derivatives such as are known from EP-B 0 255 639. For example, for the oxydehydrogenation of isobutyric acid or its esters, catalysts containing Mo, P, and V as well as Cu or Cu and Cs and which advantageously are prepared from the heteropolyacids described, have proved particularly useful.

COMBUSTIBLE FIBERS

To prepare the improved catalyst particles according to the invention, the fibers which are combustible by calcination in the temperature region from 100° C. to 380° C. and in this way leave behind channels in their stead, are well mixed with the catalytically active material, as well as with optional further additives such as known inorganic and/or inorganic auxiliaries, e.g. fillers, binders, or lubricants, or the water soluble oligomers or polymers known as additives from DE-A 37 10 784, before solidification into discrete particles and advantageously in the presence of water. Indeed, the catalytically active material may even still be present in aqueous solution when admixed with the fibers, for example. These fiber-containing mixtures, often slurrylike, are then brought into a desired shape having desired dimensions by compressing into pellets or by extrusion into rod-like particles. However, the fiber-containing mixtures can also be introduced into the cavities of shaped, and particularly of large-pored, inert carriers, such as, for example, the spherical silicon carbide carriers commercially available from Norton as "CRYSTOLON C, SC 5232", having a porosity of 40–45 percent, an interior surface area of 0.01–0.3 m²/g, and a chemical composition of 65.8 percent by w SiC and 28.5 percent by weight of $SiO_2$, in which case a special operational step for particle formation is obviated.

For the creation of the channels in the catalysts of the invention, both natural and also synthetic organic fibers (textile fibers) are useful, as are carbon fibers which are formed by the carbonization and graphitization of natural and synthetic organic fibers, i.e. those comprising carbon compounds. They are destroyed on calcination in the temperature region from 100° C. to 380° C., particularly in the presence of oxygen and are finally decomposed to gaseous products, leaving behind cavities which correspond practically with the dimensions of the fibers previously present. As natural fibers, cotton, wool, and cellulose are exemplary, for instance, and materials such as polyamides (nylon), polyester, polyolefins, or acrylonitrile are used as synthetic organic fibers.

The fibers to be used according to the invention have diameters from 1 to 100 microns, particularly diameters from 5 to 70 microns, and especially diameters from 15 to 50 microns, and lengths which can be multiples of the diameters of the final catalyst particles, for example from 1 to 30 mm, preferably 1 to 10 mm, particularly from 2 to 8 mm, and especially from 3 to 6 mm, and are added in amounts from 0.5 to 5 percent by weight, particularly from 1 to 4 percent by weight, and especially from 1.5–3.5 percent by weight based on the catalytically active material present in the catalyst.

The shaped bodies which contain the catalyst and fibers, which bodies have diameters or lengths from 1 to 10 mm, especially from 2 to 8 mm, and particularly from 3 to 6 mm, are, if necessary, dried at temperatures of 100° C. and are then further calcined by treatment at temperatures above 100° C., particularly in the region from 200° C. to 380° C., especially in the region from 250° C. to 350° C., with oxygen or gases containing oxygen, especially in the presence of air. This treatment of the shaped catalyst bodies can be carried out in an apparatus designed specially for calcination, e.g. a rotating tubular oven, but it can also be performed in the reactor, e.g. in a bundled tubular reactor, in which the catalytic oxidation reactions or oxydehydrogenation reactions are carried out with the catalyst according to the invention.

The invention is significant for the preparation of selective and active oxidation catalysts which are used in gas phase oxidation reactions in the temperature region from 200° C. to 400° C., especially for the oxidation of olefins such as propylene or isobutylene to acrolein or methacrolein, or for their further oxidation to acrylic acid or methacrylic acid. Catalysts according to the present invention have particular significance for the oxidative dehydrogenation of isobutyric acid or its lower alkyl esters to methacrylic acid or its lower alkyl esters, which reactions are advantageously performed on catalysts comprising heteropolyacids of molybdenum and also salts of these heteropolyacids. The oxydehydrogenation, for example of isobutyric acid, but also that of its lower alkyl esters, is carried out on these catalysts in a temperature region from about 250° C. to 400° C. in the presence of 1 to 4 moles of oxygen per mole of isobutyric acid, wherein further inert gases such as nitrogen, steam, or $CO_2$ inter alia can be present.

A better understanding of the invention and of its many advantages will be had from the following Examples, given by way of illustration.

In the Examples improved catalysts according to the invention, i.e. active and especially selective P-Mo-V-containing heteropolyacid catalysts, are described in the oxydehydrogenation of isobutyric acid to methacrylic acid in comparison to catalysts of the state of the art.

The dwell time and, thus, the reciprocal of the catalyst loading, is quantified by the quotient W/F, having the dimension of hours (h), wherein W is the weight of the catalytically active mass and F is the weight of the substance to be converted per hour, in this case isobutyric acid, expressed in the same weight units.

EXAMPLES

EXAMPLE 1

A catalyst containing 70 percent by weight of $Cu_{0.2}H_{3.6}PMo_{11}VO_{40}$ and 29 percent by weight of kieselguhr with 1 percent by weight of silica gel ("Aerosil") as a carrier, was extruded after the addition of 25 percent by weight of microcrystalline cellulose ("Avicel") as a pressing auxiliary and various fibers of polypropylene or viscose (each 0.5 percent by weight based on the catalyst mass). The catalyst prepared in this manner and tempered for 5 hours in air at 300° C. was used in the oxydehydrogenation of isobutyric acid in the gas phase. The components of the gas mixture of isobutyric acid, oxygen, and nitrogen led over this catalyst were respectively in a molar ratio of 1 : 1.5 : 7.71. The temperature of the catalyst was 360° C. and W/F=0.8 h.

| Catalyst*) | Conversion IBA (%) | MA | $CO_2$ | CO | Prpn | Actn | AcA | Yield MA (g/h) |
|---|---|---|---|---|---|---|---|---|
| No fibers[1] | 89.3 | 74.2 | 6.0 | 5.8 | 2.7 | 8.8 | 2.6 | 344 |
| Polypropylene[2] fibers | 82.4 | 76.9 | 4.3 | 4.4 | 4.1 | 9.7 | 0.7 | 377 |
| Viscose[3] fibers | 80.9 | 75.5 | 4.9 | 5.3 | 2.9 | 10.5 | 0.9 | 299 |

MA = methacrylic acid
IBA = isobutyric acid
Prpn = propene
Actn = acetone
AcA = acetic acid
*) Interior surface area:
[1] 1.9 $m^2/g$
[2] 2.0 $m^2/g$
[3] 2.1 $m^2/g$

EXAMPLE 2

The catalyst was prepared as in Example 1 and extruded with fibrous material. The catalyst so made and tempered at 300° C. for 5 hours in an oxygen atmosphere was used in the oxydehydrogenation of isobutyric acid in the gas phase. The components of the gaseous mixtures of isobutyric acid, oxygen, and nitrogen led over this catalyst stood respectively in a molar ratio of 1 : 1.3 : 22. The temperature of the catalyst was so chosen that a constant conversion of about 86 percent ±1 was achieved. W/F=1.0 h.

| Catalyst | Temp (°C.) | Cnvrsn IBA (%) | Selectivities | | | | | | Yield MA (g/h) |
|---|---|---|---|---|---|---|---|---|---|
| | | | MA | $CO_2$ | CO | Prpn | Actn | AcA | |
| No fibers | 330 | 86.8 | 80.4 | 3.8 | 4.5 | 1.8 | 8.9 | 0.5 | 290 |
| Polypropylene fibers | 350 | 85.6 | 83.6 | 3.2 | 3.9 | 2.3 | 6.4 | 0.6 | 341 |
| Viscose fibers | 350 | 86.6 | 81.9 | 3.5 | 3.9 | 2.3 | 8.4 | 0.0 | 277 |

MMA = methacrylic acid
IBA = isobutyric acid
Prpn = propene
Actn = acetone
AcA = acetic acid

EXAMPLE 3

The catalyst was prepared as in Example 1 and extruded with fiber material. The catalyst so prepared and calcined in an oxygen atmosphere for 5 hours at 300° C. was used in the oxydehydrogenation of isobutyric acid in the gas phase. The components of the gaseous mixture of isobutyric acid, water, oxygen, and nitrogen led over this catalyst stood respectively in a molar ratio of 1 : 2 : 1 : 16. The temperature of the catalyst was so chosen that a constant conversion of about 85±2 percent was achieved. W/F=2.0 h.

| Catalyst | Temp (°C.) | Conversion IBA (%) | Selectivities | | | | | | Yield MA (g/h) |
|---|---|---|---|---|---|---|---|---|---|
| | | | MA | $CO_2$ | CO | Prpn | Actn | AcA | |
| No fibers | 318 | 86.6 | 73.9 | 4.9 | 5.8 | 2.4 | 11.4 | 1.6 | 133 |
| Polypropylene fibers | 323 | 84.6 | 76.9 | 4.0 | 4.7 | 3.4 | 10.5 | 0.6 | 155 |
| Viscose fibers | 325 | 83.0 | 75.3 | 4.5 | 5.5 | 2.8 | 11.6 | 0.4 | 122 |

MMA = methacrylic acid
IBA = isobutyric acid
Prpn = propene
Actn = acetone
AcA = acetic acid A catalyst of 70 percent by weight of $Cu_{0.2}H_{3.6}PMo_{11}VO_{40}$ and 30 percent by weight of kieselguhr and silica gel ("Aerosil 200 or OX50", ratio 29 : 1 to 5 : 1) as a carrier, was granulated with viscose fibers (0.5 percent by weight of the catalyst mass) or with 2 percent by weight of graphite as a conventional additive for shaping. The catalyst prepared in this way and tempered for 5 hours at 300° C. in air was used in the gas phase oxydehydrogenation of isobutyric acid. The components of the gaseous mixture of isobutyric acid, oxygen, and nitrogen led over this catalyst stood respectively in a molar ratio of 1 : 1.5 : 7.71. The temperature of the catalyst was 360° C. and W/F=0.8 h.

| Catalyst*) | Conversion IBA (%) | Selectivities | | | | | | Yield MA (g/h) |
|---|---|---|---|---|---|---|---|---|
| | | MA | $CO_2$ | CO | Prpn | Actn | AcA | |
| Kieselguhar/ "Aerosil 200" (29:1) Viscose[1] fibers | 89.3 | 77.6 | 5.0 | 5.2 | 3.5 | 7.2 | 1.6 | 499 |
| Kieselguhr/ "Aerosil 200" (29:1) No fibers[2] | 91.2 | 74.0 | 5.4 | 6.4 | 3.7 | 8.4 | 2.1 | 420 |
| Kieselguhr/ "Aerosil 200" (29:1) No fibers[3] | 88.2 | 76.7 | 4.7 | 5.4 | 3.3 | 8.5 | 1.4 | 454 |
| Kieselguhr/ "Aerosil 200" (5:1) No fibers[4] | 89.2 | 76.2 | 4.8 | 5.1 | 3.9 | 8.6 | 1.4 | 423 |

MMA = methacrylic acid
IBA = isobutyric acid
Prpn = propene
Actn = acetone
AcA = acetic acid
*)Interior surface area:
[1] 2.0 m²/g
[2] 1.9 m²/g
[3] 1.7 m²/g
[4] 2.1 m²/g

What is claimed is:

1. The method for making a shaped body of a catalyst suitable for gas phase oxidation reactions, which method comprises admixing a catalytically active material of the formula $$H_a M_b P_c Mo_d V_e O_f,$$

wherein M is at least one metal ion selected from the group consisting of Li, Na, K, Rb, Cs, Mg, Ca, Zn, Al, Ce, Ti, Zr, Sn, Sb, As, Bi, Cr, Mn, Fe, Sn, Ni, and Cu, a is a number from 0 to 8, b is a number from 0 to 6, c is a number from 1 to 2, d is a number from 9 to 12, e is a number from 0.2 to 3, and f is a number the value of which satisfies the stoichiometry of the material as determined by the valencies and amounts of the remaining elements, with from 0.5 to 5 percent, by weight of the catalytically active material, of carbon fibers or organic fibers having a length from 1 to 30 millimeters and a diameter from 1 to 100 microns, imparting shape to the resulting mixture to form a shaped body, and then removing said fibers from said shaped body by calcining the shaped body at a temperature from 100° C. to 380° C. in the presence of oxygen, whereby channels are formed in the shaped body.

2. A method as in claim 1 wherein natural or synthetic organic fibers are admixed with said catalytically active material and are removed by calcining.

3. A method as in claim 1 wherein the interior surface area of the calcined shaped body is oil to 5 $m^2/g$.

4. A catalyst made by the method of claim 1.

5. A catalyst made by the method of claim 2.

6. A catalyst made by the method of claim 3.

7. A method as in claim 1 wherein the fibers have a length from 1 to 10 millimeters.

8. A catalyst made by the method of claim 7.

* * * * *